United States Patent [19]

Alexander et al.

[11] Patent Number: 5,055,446

[45] Date of Patent: Oct. 8, 1991

[54] METHOD TO IMPROVE SURVIVAL OF PATIENTS DURING SEPSIS BY DIET COMPOSITION

[75] Inventors: J. Wesley Alexander; Michael D. Peck, both of Cincinnati, Ohio

[73] Assignee: University of Cincinnati, Cincinnati, Ohio

[21] Appl. No.: 260,880

[22] Filed: Oct. 21, 1988

[51] Int. Cl.[5] .................... A61K 37/00; A61K 31/70; A61K 31/23

[52] U.S. Cl. .......................... 514/2; 514/23; 514/552

[58] Field of Search .............................. 514/552, 23, 2

[56] References Cited

U.S. PATENT DOCUMENTS 4,101,673  7/1978  Chang ................................. 424/312
4,474,773  10/1984  Shinitzky et al. .................. 424/199
4,820,731  4/1989  Mascioli et al. ..................... 514/552

OTHER PUBLICATIONS

Yoskikawa et al., Mie Med. Journ., vol. XXXV, No. 1, Issued 1985 pp. 95–100.
Alexander: Annals of Surgery, vol. 204, No. 1, Jul. 1986, pp. 1–8.
Thomas et al., J. Nutr., vol. 115, 15-28-1534, 1985.
Mascioli et al.: Am. J. Clin. Nutr., 1989:49:277–82, 1989.
Yoshikawa et al.: Mie Med. Journ., vol. XXXV, No. 1, Issued 1985, pp. 95–100, "Resistance to Opportunistic Infections . . . ".
Dayton et al.: J. Nutri., vol. 107, issued 1977, pp. 1353–1360, "Effect of High-Oleic and High-Linoleic Safflower Oils . . . ".
Shils et al.: Modern Nutrition in Health and Disease, 7th Edition, 1988.

*Primary Examiner*—Frederick E. Waddell
*Assistant Examiner*—Zohreh A. Fay
*Attorney, Agent, or Firm*—Wood, Herron & Evans

[57] ABSTRACT

Septic patients are treated with an enteral or parenteral diet that improves mortality rate of the septic patients. The diet which is designed to provide the total caloric intake for the septic patient includes an low concentration of calories provided by protein. Generally from about 4% to about 10% of the calories in the diet are provided by protein. More preferably no more than 5% of the calories are provided by protein. The remainder of the diet is formed from lipids, and carbohydrates. The lipids should be in the form of a combination of omega 6 and omega 3 fatty acids. The diet will also include a vitamin and mineral supplement.

3 Claims, No Drawings

METHOD TO IMPROVE SURVIVAL OF PATIENTS DURING SEPSIS BY DIET COMPOSITION

Research leading to the present invention was funded in part by the National Institute of Health. Therefore the federal government is hereby granted an irrevocable, royalty free, non-exclusive license to practice the present invention.

BACKGROUND OF THE INVENTION

There has been relatively little research conducted to demonstrate the effect of diet on patients during sepsis. Many factors are known about metabolism during sepsis for example there is a major increase in whole body protein catabolism during sepsis that is only slightly offset by a minor increase in protein synthesis. The resulting increase in net protein catabolism produces increased excretion of nitrogen as clinically manifested by muscle wasting and weight loss.

In order to prevent these losses of body proteins during sepsis aggressive nutrition support has been advocated to restore positive nitrogen balance. There are little data regarding the optimum amount of protein necessary for recovery from sepsis.

Skeletal muscle wasting and weight loss become clinically evident as sepsis progresses. Nutritional recommendation for septic patients uniformly include increased calories and protein. Certain researchers suggest 1.5 to 2.5 grams of protein per kilogram body weight per day for the moderately stressed patient and 3 grams of protein per kilogram body weight per day for the maximally catabolic patients.

However, there are no data that correlates the amount of protein given to survival rate. The goal of the medical community to date has been simply to supply protein until a positive nitrogen balance has been restored. It was found that total parenteral nutrition solutions that infuse protein at a mean rate of 1.46 grams per kilogram body weight per day in 17 septic patients reduced net protein catabolism from 2.20 grams per kilogram body weight per day to 0.63 grams of kilogram body weight per day. Increasing the rate of protein delivery from 1.1 grams per kilogram per day to 2.2 grams per kilogram per day produced no additional decrease in protein catabolism. In fact, optimal protein sparing was noted at 1.5 kilograms protein per kilogram per day.

It has been shown that protein calorie malnutrition increases the risk of infection. Experimental studies of short term protein deprivation in animals have produced inconsistent results. Conclusions that can be drawn from experimental studies include the observation that resistance to bacterial challenge is diminished by chronic protein restriction. In addition bacterial activity is generally unchanged. Depression of delayed type hypersensitivity has also been confirmed in animal studies.

It has been further shown that diet can affect the immune response system after major assaults to the body. For example, in The Importance of Lipotype in the Diet After Burn, *Anals. of Surgery*, Vol. 204 No. 1, July 1986 it is reported that the lipids contained in the diet have an effect on the immune response system in burn patients. Specifically, it reports that a diet high in omega 6 fatty acids such as linoleic acid have a significant immunosuppressive effect. On the other hand, diets high in omega 3 fatty acids improve the immune response system. In "The Effect of Dietary Unsaturated Fatty Acids And Indomethacin on Metabolism and Survival After Burn" it is reported that excessive dietary polyunsaturated linoleic acid may influence immunocompetence after burn. In a co-pending application invented by the inventors of the present invention filed Oct. 4, 1988 entitled Method to Improve Immune Response and Resistance to Infection Following Surgery by Diet there is disclosed a presurgery diet composition designed to reduce the risk of infection. The diet is high in omega 6 fatty acids.

Unfortunately none of the diets currently administered to septic patients are designed to have an effect on the infection. They are primarily designed to counter the metabolic effect of sepsis and accordingly may not contribute to the survival rate of the patient.

SUMMARY of THE INVENTION

The present invention is premised on the realization that sepsis can be treated in part by diet. By providing a patient with a diet very low in protein the sepsis condition is improved and the survival rate of the patient is improved.

More specifically, the present invention is premised on the realization that providing a septic patient with a diet having only from about 4 to less than about 10% of its total calories provided by protein substantially improves the survival rate of septic patient. The diet increases the negative nitrogen content. Although protein catabolism may result in a net loss of total skeletal muscle mass, the survival rate surprisingly is improved by actually treating the sepsis.

The present invention will be further appreciated in light of the following detailed description.

DETAILED DESCRIPTION OF THE INVENTION

Septic patients are fed a diet which contains from about 4 to about less than 10% of its total calories from proteins with from about 30 to 40% of the non-protein calories provided by lipids and from about 50 to about 70% of non-protein diets provided by carbohydrates. The diet will also include a source of a mineral and vitamin supplement.

The diet which can either be designed to be a parenteral diet or an enteral diet depending on the patient and will generally be an aqueous emulsion of protein, carbohydrate and fat along with vitamin and mineral sources. The total calories of the diet which should be ingested by the patient will be from about 20 to about 50 kilocalories per kilogram body weight per day. The total energy needs vary according to the individual. It is generally ill-advised to provide excessive calories for septic patients.

The total calories of the diet will be derived from the carbohydrates, the proteins and the fat. Generally it is desirable that from about 4 to less than about 10% of the total calories be provided by the protein. Preferably only about 5% of the calories should be provided by protein. For an enteral diet suitable sources of protein would include milk proteins, soy proteins, and others.

For a parenteral diet a combination of amino acids should be employed instead of the more complex protein. For purposes of the present invention, protein is intended to include amino acids. These amino acids can include leucine, lysine, valine, isoleucine, phenylalanine, threonine, methionine, histidinine and tryptophane. These are considered the essential amino acids. Other non-essential amino acids can include glutamic acid, proline, aspartic acid, serine, arginine, alanine, glycine, glutamine and tyrosine. These are considered the non-essential amino acids. These would be provided generally in a total parenteral nutrition diet.

Further from about 50 to 70% of the nonprotein calories (about 45-65% of the total calories) of the diet should be provided by a carbohydrate source. A wide variety of simple sugars can be used as a source of carbohydrates such as for example dextrose, fructose, sucrose and the like in combinations. Enteral diets preferably would include complex carbohydrates such as corn starch and dextrins.

From 30 to about 50% of the non-protein calories of the diet should be derived from lipids (about 25-50% of the total calories). A combination of omega 3 and omega 6 fatty acids should be employed. A diet containing only omega 3 fatty acids has certain deleterious effects. Accordingly at least about 30% and preferably 50 to 70% of the lipids should be omega 6 fatty acids. A good source of linoleic acid which is the primary omega 6 fatty acid is safflower oil which generally contains about 70% linoleic acid.

In addition to the protein, carbohydrate and fatty acid the diet should include a source of vitamins as well as minerals. The diet should include about 50 IU per day of vitamin E, 5,000-10,000 IU micrograms retinol equivalents vitamin A per day, 400 IU per day vitamin D, 1-5 grams per day vitamin C, 0.4 milligrams of folic acid per day, 20 milligrams per day of niacin, 20 milligrams per day of riboflavin, 1.5 milligrams per day of thiamine, 2 milligrams per day of vitamin B6, 3 micrograms per day of vitamin B12, 1.5 grams per day of calcium, 1.5 grams per day of phosphorous, 150 micrograms per day of iodine, 10 milligrams per day of iron, 400 milligrams per day of magnesium.

An exemplary enteral formulation of the present invention is an aqueous mixture which includes the following:

Whey Protein: 5% total calories 12.5 gm/l
Safflower Oil: 50% total calories 55.6 gm/l
Dextrins: 45% total calories 112.5 gm/l
Vitamin A: 5,000 micrograms retinol equivalents per liter
Vitamin D: 2,000 IU per liter
Vitamin E: 50 IU per liter
Vitamin C: 2 grams per liter
Folic acid: 200 micrograms per liter
Niacin: 10 milligrams per liter
Riboflavin: 1 milligram per liter
Thiamine: 750 micrograms per liter
Vitamin B6: 1 milligram per liter
Vitamin B12: 1.5 micrograms per liter
Calcium: 750 milligrams per liter
Phosphorous: 750 milligrams per liter
Iodine: 75 micrograms per liter
Iron: 5 milligrams per liter
Magnesium: 200 milligrams per liter.

This diet has a caloric content of about 1,000 calories per liter. This diet is administered to a septic patient as long as the sepsis condition continues.

Sepsis refers to a major bacteriological, viral or fungal infection which poses serious threat to the survival of the patient. The diet is provided generally as a sole form of nutrition to the patient for as long as the sepsis condition continues, but for no longer than 14 days.

In order to demonstrate the efficacy of the present invention guinea pigs with peritonitis were fed various enteral diets. This is further explained by the following example.

Example

Hartley guinea pigs weighing 350 to 450 grams were provided with intragastric feeding tubes by surgical placement. Under general anesthesia the abdomen, neck and intrascapular areas were clipped to removed hair and painted with providene iodine. A gastrostomy was performed. The free end of the tube was tunneled subcutaneously around the left hemithorax to exit via a stab wound in the upper intrascapular region later to be connected to the diet infusion system. The tube was flushed with saline and capped. For one week the animals were caged individually, taking guinea pig pellet diet (Wayne Feeds Research Division) and water ad libitum. This allowed time to more than regain the 10% body weight which occurred immediately after surgery.

After stabilization the animals underwent a laparotomy under general anesthesia to place a bacteria filled osmotic pump into the right lower quadrant to keep the pump away from the gastrostomy. The guinea pigs were then placed into individual metabollic cages and allowed to eat ad libitum for three days.

For eighteen hours prior to implantation of the pump cultures of *E coli* 53104 and *Staph aureus* 502A were each incubated in trypticase soy broth in a 37° C. oscillating water bath. The cultures were centrifuged at 2,000 rpm for 5 minutes and the resulting pellets were washed in 0.9% sodium chloride. After the final wash the pellets were serially diluted in sterile saline to achieve a final concentration of $2 \times 10^8$ bacteria per ml. An equal mixture was then made containing $1 \times 10^8$ each of *E.coli* and *Staph.aureus*.

Using aseptic techniques the osmotic pumps (Alzet Osmotic Pump, Model 2ML1) were filled with 2 ml of the *E.coli* and *Staph.aureus* mixture. To the bottom of the flow moderator a small amount of silicon bonding adhesive was added and the flow modulator was placed into the pump. Excess silicon was removed by wiping with a sterile gauze sponge. The silicon was added to create a seal between a flow moderator and the osmotic pump through which bacteria could not escape.

The copolymer cap was then removed and to the exposed stainless steel tube, a coil of sterile silicon tubing 100 cm in length was attached. The coil was secured with 3-0 sutures. The filled pumps with coil were then set aside for 20 minutes to dry and then they were implanted as previously described.

The volume of tubing was 0.35 ml and there was a residual of 1.02 ml in the spent pump. Thus, total delivery from each pump was 1.602 ml. After approximately a four hour delay after implantation the pumps began delivery of the reservoir content into the tubing. The pumps had a flow delivery rate of 0.00963 ml per hour and began actual delivery of bacteria into the peritoneal cavity between 34 and 36 hours after implantation. Thus, the pumps delivered a continuous infusion of bacteria for 6.93 days ending approximately 8.5 days after implantation.

On day 3 after implantation the animals were placed into groups and fed separate diets wherein approximately 5%, 10%, 15%, and 20% respectively of the total calories were from protein. The diets for each of these groups is set out in Table I. The amount of protein given as whey protein (Promix RPD) was 1.57 grams per kilogram body weight per day in the 5% group, 3.24 grams per kilogram body weight per day in the 10% group, 4.71 grams per kilogram body weight per day in the 15% group, and 6.28 grams per kilogram body weight per day in the 20% group. The total number of calories delivered was 125 kilocalories per kilogram body weight per day.

TABLE I

| | Experimental Diets | | | |
|---|---|---|---|---|
| | 5% | 10% | 15% | 20% |
| Protein (cal/liter) | 50.23 | 103.72 | 150.73 | 201.00 |
| Fat (cal/liter) | 151.31 | 150.09 | 147.94 | 150.75 |
| Carbohydrates (cal/liter) | 827.42 | 773.19 | 735.39 | 696.25 |
| Total (cal/liter) | 1028.97 | 1026.99 | 1034.06 | 1048.00 |
| % Protein | 4.9 | 10.1 | 14.6 | 19.2 |
| Protein (gm/KG/Day) | 1.57 | 3.24 | 4.71 | 6.28 |
| Protein (gm/M$^2$/Day) | 17.9 | 37.0 | 53.8 | 71.8 |

The composition of the basic diet is shown in Table II. To arrive at the experimental diets, the amount of protein was reduced and carbohydrates increased. They were fed for 14 days via the gastrostomy by continuous pump controlled infusion. All animals received equivalent volumes of fluid daily by diluting the daily diet with tap water based on previously calculated fluid requirements.

TABLE II

| Composition of Basic Diet | |
|---|---|
| Nutrient Sources | |
| protein (Promix R.P.D.[1]) | 3.85 cal/gm |
| fat (Microlipid[2]) | 4.5 cal/cc |
| carbohydrate (Nutrisource[3]) | 3.2 cal/cc |
| Electrolyte and Vitamin Solution | |
| NaCl (2.5 mEq/ml) | 24 ml |
| KCl (2 mEq/ml) | 10 ml |
| K acetate (2 mEq/ml) | 24 ml |
| K phosphate (3 mM/ml) | 10 ml |
| Ca gluconate (0.1 Gm/ml) | 24 ml |
| MgSO4 (4 mEq/ml) | 24 ml |
| MTE5[4] | 6 ml |
| MVI Concentrate[5] | 5 ml |
| Vitamin C | 500 mg |
| Vitamin E | 100 mg |
| Choline Chloride | 500 mg |
| Folic Acid | 2 mg |

[1] Navaco Laboratories, Phoenix, AZ
[2] Organon, Inc., (Bioresearch), West Orange, NJ
[3] SandozNutrition, Minneapolis, MN
[4] Each ml of MTE-5 provides in a 400 gm animal:
zinc       1 mg      1050 mg/kg/day
copper     0.4 mg    420 mg/kg/day
manganese  0.1 mg    0.150 mg/kg/day
chromium   4 mcg     4.2 mg/kg/day
selenium   20 mcg    21 mg/kg/day
[5] USV Laboratories, Tuckahoe, NY The animals were weighed daily at the same time of day throughout the experiment without stopping the continuous feeding. All animals surviving 14 days after the start of the diet (17 days after pump implantation) were sacrificed by cervical dislocation following phlabotomy by cardiac puncture. Wet weight of the carcass consisting of skeletal and musculofacial structures was measured after the animal had been completely skinned, eviserated and decapitated and the feet excised.

Samples of serum from normal guinea pigs which had not undergone manipulation were used as controls for comparison. Serum albumine, transferrin and $C_3$ were determined using a colorimetric method on a spectrophotometer. Serum cortisol was determined using fluorescence polarization immunoassay with mouse and goat antisera on a TDX analyzer. Serum free amino acids were determined using a Beckman 121-MP amino acid analyzer. Urine nitrogen was measured using the Antech Pyrochema Luminescent nitrogen system involving an oxidative paralysis of the specimen and subsequent measurement of the chemiluminescence of $NO_2$. Calculated daily urinary nitrogen excretion was then subtracted from the amount of nitrogen administered enterally and the difference taken as the nitrogen balance.

Albumin was significantly lower in all experimental groups compared to normal control animals. There was, however, no significant difference in level of transferrin, $C_3$ and cortisol.

Amino acid assays showed a significant decrease in most experimental groups compared to control of citrulline, glycine, isoleucine, leucine, ornithine, proline, serine, threonine, tryptophan, tyrosine and valine. Compared to the 10% group sistine was lower in the control group. Levels of the other 10 amino acids measured remained the same.

The mean daily nitrogen balance between groups was $-163.5$ plus or minus 10 grams in the 5% group, $-114.6$ plus or minus 12.2 grams in the 10% group, $-57.1$ plus or minus 17.2 grams in the 15% group and $+43.3$ plus or minus 14.6 grams in the 20% group. Multiple regression analysis of the variable protein group, day of infection and ultimate outcome showed that neither day of infection nor ultimate outcome were significantly correlated with nitrogen balance. Using stepwise regression to eliminate these variables from the equation, protein group was found to correlate significantly although weakly with nitrogen balance. This linear relationship can be described by the equation nitrogen balance $= -240.421 + 67.312$ (% protein in diet).

Most telling was the mortality rate of the tested animals. The survival rate was 11/24 (46%) in the 5% group, 6/26 (23%) in the 10% group, 3/25 (12%) in the 15% group and 4/26 (15%) in the 20% group. These differences are significant using the total $Chi^2$ analysis ($p=0.0247$). Analysis of pairs of groups show the mortality was significantly higher in the 15% and 20% group compared to the 5% group ($p=0.0212$ and $p=0.415$ respectively).

Thus the results indicate that the guinea pigs maintained on low protein enteral diets (1.5 grams per kilogram body weight per day) during bacterial peritonitis have improved survival. Healthy guinea pigs require 11–18% natural protein in diets (NRC 1978). We have shown that sham operated 400 gram guinea pigs eat approximately 17 grams of natural chow daily, resulting in consumption of over 7 grams of protein per kilogram body weight per day. The protein restriction represented by the 5% diet may have improved survival either through modulation of the immune response or by an effect of bacterial virulence. These results demonstrate clearly that providing a low protein diet significantly reduces the mortality of septic patients.

The preceding has been a description of the present invention as well as the preferred mode of practicing the invention currently known to the inventors. However the scope of the invention should be defined by the following claims:

We claim:

1. A method of treating septic patients comprising: administering to said patients a diet during sepsis condition, said diet having about 20-50 kilocalories per kilogram body weight and wherein less than about 10% of the calories in said diet are derived from protein; and
wherein said diet further comprises from about 30 to about 50% lipids based on total calories and from about 45 to about 54% carbohydrates based on total calories.

2. The method claimed in claim 1 wherein said diet further includes a vitamin supplement and a mineral supplement.

3. The method of treating septic patients claimed in claim 1 wherein said diet includes from about 30% to about 50% lipids based on total calories and wherein 50% to 70% of said lipids are omega-6 fatty acids.

* * * * *